(12) United States Patent
Strom et al.

(10) Patent No.: US 7,347,995 B2
(45) Date of Patent: Mar. 25, 2008

(54) COMPOSITIONS AND METHODS FOR ACHIEVING IMMUNE SUPPRESSION

(75) Inventors: Terry B. Strom, Brookline, MA (US); Wlodzimierz Maslinski, Warsaw (PL); Xin Xiao Zheng, Brookline, MA (US); Yon Su Kim, Seoul (KR); Sylvie Ferrari-Lacraz, Geneva (CH)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 356 days.

(21) Appl. No.: 10/853,466

(22) Filed: May 25, 2004

(65) Prior Publication Data

US 2004/0219148 A1 Nov. 4, 2004

Related U.S. Application Data

(62) Division of application No. 09/855,313, filed on May 14, 2001, now Pat. No. 6,797,263.

(60) Provisional application No. 60/203,801, filed on May 12, 2000.

(51) Int. Cl.
*C07K 14/54* (2006.01)
*C07K 14/435* (2006.01)
*A61K 38/00* (2006.01)
*A61K 38/20* (2006.01)

(52) U.S. Cl. .................. 424/85.1; 424/85.2; 435/69.5; 435/69.52; 435/69.7; 435/71.1; 530/351

(58) Field of Classification Search ..................... None
See application file for complete search history.

(56) References Cited

U.S. PATENT DOCUMENTS

| | | | |
|---|---|---|---|
| 5,116,964 A | 5/1992 | Capon et al. | |
| 5,552,303 A | 9/1996 | Grabstein et al. | |
| 5,574,138 A | 11/1996 | Grabstein et al. | |
| 5,707,616 A | 1/1998 | Grabstein et al. | |
| 5,747,024 A | 5/1998 | Grabstein et al. | |
| 5,892,001 A | 4/1999 | Grabstein et al. | |

FOREIGN PATENT DOCUMENTS

| | | |
|---|---|---|
| DE | 19823351 A1 | 12/1998 |
| WO | WO 88/07089 | 9/1988 |
| WO | WO 93/08207 | 4/1993 |
| WO | WO 93/19770 | 10/1993 |
| WO | WO 94/04180 | 3/1994 |
| WO | WO 94/04570 | 3/1994 |
| WO | WO 94/17773 | 8/1994 |
| WO | WO 95/06480 | 3/1995 |
| WO | WO 95/06481 | 3/1995 |
| WO | WO 95/06666 | 3/1995 |
| WO | WO 95/27722 | 10/1995 |
| WO | WO 95/28957 | 11/1995 |
| WO | WO 96/16665 | 6/1996 |
| WO | WO 96/23071 | 8/1996 |
| WO | WO 96/26274 | 8/1996 |
| WO | WO 9626274 A | 8/1996 |
| WO | WO 96/40246 | 12/1996 |
| WO | WO 97/17446 | 5/1997 |
| WO | WO 97/20063 | 6/1997 |
| WO | WO 97/22256 | 6/1997 |
| WO | WO 97/26000 | 7/1997 |
| WO | WO 97/34633 | 9/1997 |
| WO | WO 9741232 A | 11/1997 |
| WO | WO 98/01145 | 1/1998 |
| WO | WO 98/52606 | 11/1998 |
| WO | WO 98/56417 | 12/1998 |
| WO | WO 98/58672 | 12/1998 |
| WO | WO 99/00143 | 1/1999 |
| WO | WO 99/12566 | 3/1999 |

OTHER PUBLICATIONS

Mijares et al, Molecular Pharmacology, 2000, vol. 58, pp. 373-379.*
Boulougouris et al, The Journal of Immunology, 1998. vol. 161, pp. 3919-3924.*
Lin, et al. *The Role of Shared Receptor Motifs and Common Stat Proteins in the Generation of Cytokine Pleiotropy and Redundancy by IL-2, IL-4, IL-7, IL-13, and IL-15.* Immunity, 2:331-339 (Apr. 1995).
Morrison, et al. *Structural Determinants of Human IgG Function.* The Immunologist 2(4):119-124 (1994).
Brekke, et al. *Structure-Function Relationships of Human IgG.* The Immunologist 2(4):125-130 (1994).
Pettit, et al. *Structure-Function Studies of Interleukin 15 using Site-specific Mutagenesis, Polyethylene Glycol Conjugation, and Homology Modeling.* The Journal of Biological Chemistry 272(4): 2312-2318 (1997).
Stevens, et al. *Interleukin-15 signal, T84 colonic epithelial cells in the absence of the interleukin-2 receptor β-chain.* Am. J. Physiol. 272:G1-G8 (1997).
Armitage, et al. *IL-15 Has Stimulatory Activity for the Induction of B Cell Proliferation and Differentiation.* Journal of Immunology 154:483-490 (1995).
Chae, et al. *Distribution of IL-15 Receptor α-Chains on Human Peripheral Blood Mononuclear Cells and Effect of Immunosuppressive Drugs on Receptor Expression.* Journal of Immunology 157:2813-2819 (1996).
Moreland, et al. *Treatment of Rheumatoid Arthritis with a Recombinant Human Tumor Necrosis Factor Receptor (p75)-Fc Fusion Protein.* N. Engl. J. Med 337(3):141-147 (1997).
Elliott, et al. *Repeated therapy with monoclonal antibody to tumor necrosis factor α(cA2) in patients with rheumatoid arthritis.* Lancet 344(8930):1125-1127 (1994).

(Continued)

Primary Examiner—Elizabeth C. Kemmerer
Assistant Examiner—Fozia Hamud
(74) Attorney, Agent, or Firm—Fish & Richardson P.C.

(57) ABSTRACT

Disclosed herein are therapeutic compositions containing agents that modulate the immune response in a patient.

17 Claims, 3 Drawing Sheets

OTHER PUBLICATIONS

Elliott, et al. *Randomized double-blind comparison of chimeric monoclonal antibody to tumour necrosis factor α(cA2) versus placebo in rheumatoid arthritis*. Lancet 344(8930):1105-1110 (1994).

Williams, et al. *Successful therapy of collagen-induced arthritis with TNF receptor-IfG fusion protein and combination with anti-CD4*. Immunology 84(3): 433-439 (1995).

Wooley, et al. *Influence of a Recombinant Human Soluble Tumor Necrosis Factor Receptor FC Fusion Protein on Type II Collagen-Induced Arthritis in Mice*. Journal of Immunology 151(11):6442-6607 (1993).

Vey, et al. *IFN-γ and 1,25(OH)$_2$D$_3$ Induce on THP-1 Cells Distinct Patterns of Cell Surface Antigen Expression, Cytokine Production, and Responsiveness to Contact with Activated T Cells*. Journal of Immunology 149(6):2040-2046 (1992).

Courtenay, et al. *Immunisation against heterologous type II collagen induces arthritis in mice*. Nature 283(5748): 666-668 (1980).

Burger, et al. *Imbalance between interstitial collagenase and tissue inhibitor of metalloproteinases I in synociocytes and fibroblasts upon direct contact with stimulated T Lymphocytes*. Arthritis & Rheumatism 41(10):1748-1759 (1998).

Kim, et al. *Targeting the IL-15 Receptor with an Antagonist IL-15 Mutant/Fcγ2a Protein Blocks Delayed-Type Hypersensitivity*. Journal of Immunology 160:5742-5748 (1998).

Li, et al. *Induction of Allograft Tolerance in the Absence of Fas-Mediated Apoptosis*. Journal of Immunology 163:2500-2507 (1999).

Kim, et al. *Targeting the IL-15 Receptor with an Antagonist IL-15/Fcγ2a Protein BlocksDTH and Enhances the Acceptance of Islet Allografts*. 17th ASTP (Physicist) Annual Meeting, Chicago, IL May 9-13, 1998 (p. 713).

Kirk, et al. *Treatment of humanized monoclonal antibody against CD154 prevents acute renal allograft rejection in nonhuman primates*. Nature Medicine 5(6):686-693 (1999).

Nickerson, et al. *Prolonged islet allograft acceptance in the absensce of interleukin 4 expression*. Transplant Immunology 4:81-85 (1996).

Lakkis, et al. *Interleukin 4 receptor targeted cytotoxicity: genetic construction and in vivo immunosuppressive activity of a diphtheria toxin-related murine interleukin 4 fusion protein*. Eur. J. Immunol. 21:2253-2258 (1991).

Li, et al. *Blocking both signal 1 and signal 2 of T-cell activation prevents apoptosis of alloreactive T cells and induction of peripheral allograft tolerance*. Nature Medicine 5(11):1298-1302 (1999).

Agostini et al., *Blood*, v93 (No. 4), pp. 1277-1286 (Feb. 1999).

Ferrari-Lacraz et al., *Jrl. Of Immuno.*, v167 (No. 6), pp. 3478-3485 (Se. 2001).

Kim et al., *Jrl. Of Immuno.*, v160 (No. 12), pp. 5742-5748 (Je. 1998).

Kim et al., *Transplantation Proceedings*, v30 (No. 8), pp. 4031-4036 (1998).

\* cited by examiner

DNA sequence   489 b.p.   atgagaatttcg ... aacacttcttga   linear

1/1
atg aga att tcg aaa cca cat ttg aga agt att tcc atc cag tgc tac ttg tgt tta ctt
Met arg ile ser lys pro his leu arg ser ile ser ile gln cys tyr leu cys leu leu
61/21 cta aac agt cat ttt cta act gaa gct ggc att cat gtc ttc att ttg ggc tgt ttc agt
leu asn ser his phe leu thr glu ala gly ile his val phe ile leu gly cys phe ser
121/41 gca ggg ctt cct aaa aca gaa gcc aac tgg gtg aat gta ata agt gat ttg aaa aaa att
ala gly leu pro lys thr glu ala asn trp val asn val ile ser asp leu lys lys ile
181/61 gaa gat ctt att caa tct atg cat att gat gct act tta tat acg gaa agt gat gtt cac
glu asp leu ile gln ser met his ile asp ala thr leu tyr thr glu ser asp val his
241/81 ccc agt tgc aaa gta aca gca atg aag tgc ttc ttg gag tta caa gtt att tca ctt
pro ser cys lys val thr ala met lys cys phe leu glu leu gln val ile ser leu
301/101 gag tcc gga gat gca agt att cat gat aca gaa aat ctg atc atc cta gca aac aac
glu ser gly asp ala ser ile his asp thr glu asn leu ile ile leu ala asn asn
361/121 agt ttg tct tct aat ggg aat gta aca gaa tct gga tgc aaa gaa tgt gag gaa ctg gag
ser leu ser ser asn gly asn val thr glu ser gly cys lys glu cys glu glu leu glu
421/141 gaa aaa aat att aaa gaa ttt ttg gac agt ttt gta cat att gtc gac atg ttc atc aac
glu lys asn ile lys glu phe leu asp ser phe val his ile val asp met phe ile asn
481/161 act tct tga    (SEQ ID NO: 1)
thr ser OPA    (SEQ ID NO: 2)

FIG. 1

```
DNA sequence    489 b.p.    atgagaatttcg ... aacacttcttga    linear
1/1
atg aga att tcg aaa cca cat ttg aga agt att tcc atc cag tgc tac ttg tgt tta ctt
Met arg ile ser lys pro his leu arg ser ile ser ile gln cys tyr leu cys leu leu
 61/21
                                                                        91/31
cta aac agt cat ttt cta act gaa gct ggc att cat gtc ttc att ttg ggc tgt ttc agt
leu asn ser his phe leu thr glu ala gly ile his val phe ile leu gly cys phe ser
121/41
                                                                        151/51
gca ggg ctt cct aaa aca gaa gcc aac tgg gtg aat gta ata agt gat ttg aaa aaa att
ala gly leu pro lys thr glu ala asn trp val asn val ile ser asp leu lys lys ile
181/61
                                                                        211/71
gaa gat ctt att caa tct atg cat att gat gct act tta tat acg gaa agt gat gtt cac
glu asp leu ile gln ser met his ile asp ala thr leu tyr thr glu ser asp val his
241/81
                                                                        271/91
ccc agt tgc aaa gta aca gca atg aag tgc ttt ctc ttg gag tta caa gtt att tca ctt
pro ser cys lys val thr ala met lys cys phe leu leu glu leu gln val ile ser leu
301/101
                                                                        331/111
gag tcc gga gat gca agt att cat gat aca gaa aat ctg atc atc cta gca aac aac
glu ser gly asp ala ser ile his asp thr val glu asn leu ile leu ala asn asn
361/121
                                                                        391/131
agt ttg tct tct aat ggg aat gta aca gaa tct gga tgc aaa gaa gaa tgt gag gaa ctg gag
ser leu ser ser asn gly asn val thr glu ser gly cys lys glu glu cys glu leu glu
421/141
                                                                        451/151
gaa aaa aat att aaa gaa ttt ttg cag agt ttt gta cat att gtc caa atg ttc atc aac
glu lys asn ile lys glu phe leu gln ser phe val his ile val gln met phe ile asn
481/161
act tct tga   (SEQ ID NO: 3)
thr ser OPA   (SEQ ID NO: 4)
```

FIG. 2

COMPOSITIONS AND METHODS FOR ACHIEVING IMMUNE SUPPRESSION

RELATED APPLICATIONS

This application is a divisional of application Ser. No. 09/855,313, filed May 14, 2001 now U.S. Pat. No. 6,797, 263, which claims the benefit of Provisional Application Ser. No. 60/203,801, filed on May 12, 2000. The entire contents of the above applications are incorporated herein by reference.

FIELD OF THE INVENTION

The field of the invention is immune suppression.

BACKGROUND OF THE INVENTION

An effective immune response begins when an antigen or mitogen triggers the activation of T cells. In the process of T cell activation, numerous cellular changes occur, which include the expression of cytokines and cytokine receptors. One of the cytokines involved in the immune response is interleukin-15 (IL-15), which is a T cell growth factor that stimulates the proliferation and differentiation of B cells, T cells, natural killer (NK) cells, and lymphocyte-activated killer (LAK) cells in vitro. In vivo, the proliferation of these cell types enhances the immune response.

Patients benefit from suppression of the immune response in a number of circumstances, for example, in the event of organ transplantation or immune disease, particularly autoimmune disease. In other circumstances, for example when select immune cells have become malignant or autoaggressive, it is beneficial to actively destroy them.

SUMMARY OF THE INVENTION

The present invention is based on the discovery of novel ways to suppress the immune response. In each case, suppression is achieved by administration of a first agent that targets an interleukin-15 receptor (IL-15R) and a second agent that blocks a costimulatory signal that is normally transmitted from antigen presenting cells (APCs) to T cells. Accordingly, the invention features methods of treating a patient who would benefit from immune suppression (e.g., a patient who has received, or is scheduled to receive, a transplant or who has an immune disease, particularly an autoimmune disease) by administering one or more agents that target an IL-15R and one or more agents that block a costimulatory signal. The invention also features therapeutic compositions that include one or more of each of the first and second agents described above. Although such compositions would necessarily contain more than one agent, the methods of the invention are not limited to those in which the agents are necessarily administered simultaneously. The agents of the invention, and methods for their use, are described below.

Many of the agents used in the context of the present invention have advantageous therapeutic characteristics. For example, agents that target an IL-15R can be fusion proteins that include a mutant IL-15 (mIL-15) polypeptide. These agents are unlikely to be immunogenic because the mutant IL-15 portion of the fusion protein can differ from wild type IL-15 by only a few substituted residues. In addition, since mIL-15 polypeptides can bind the IL-15Rα with the same high affinity as wild type IL-15, they can compete effectively for the receptor. Further, agents of the invention can activate components of the host immune system, such as complement and phagocytes, that ultimately mediate an elimination, i.e. depletion, of cells bearing the receptor to which the agent binds (by, e.g., mediating lysis or phagocytosis of targeted cells). As the alpha subunit of the IL-15 receptor (IL-15Rα) is expressed by activated or malignant immune cells, but not by resting immune cells, agents of the invention can be used to specifically target those cells that have been activated (e.g., antigen-activated T cells) or that have become malignant. A further advantage of the invention is that when an agent that targets an IL-15R is administered with an agent that blocks a costimulatory signal, tolerance is induced. Consequently, immunosuppression can be discontinued without the graft being rejected or secondary grafts can be accepted without further immunosuppression.

Other features and advantages of the invention will be apparent from the following detailed description and from the claims. Although materials and methods similar or equivalent to those described herein can be used in the practice or testing of the invention, the preferred materials and methods are described below.

BRIEF DESCRIPTION OF THE DRAWINGS

FIG. 1 is a representation of a mutant IL-15 nucleic acid sequence (SEQ ID NO:1) and the predicted amino acid sequence (SEQ ID NO:2). The wild-type codon encoding glutamine at position 149, CAG, and the wild-type codon encoding glutamine at position 156, CAA, have both been changed to GAC, which encodes aspartate. (These positions (149 and 156) correspond to positions 101 and 108, respectively, in the mature IL-15 polypeptide, which lacks a 48-amino acid signal sequence).

FIG. 2 is a representation of a wild-type IL-15 nucleic acid sequence (SEQ ID NO:3) and the predicted amino acid sequence (SEQ ID NO:4).

DETAILED DESCRIPTION

Figure 3:
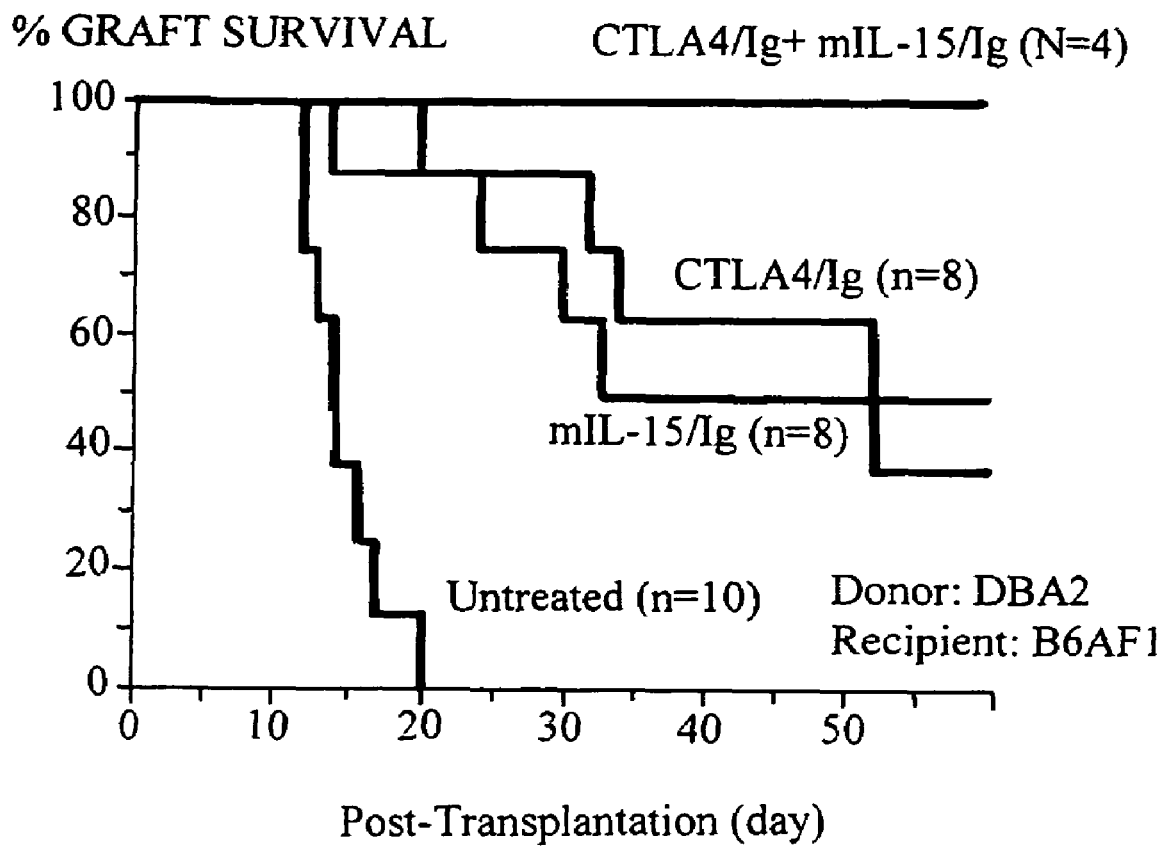
FIG. 3 is a line graph depicting the percentage of graft survival after transplantation of islet cells from donor DBA2 mice to recipient B6AF1 mice. The recipients were either untreated or treated with mIL-15/Ig, CTLA4/Ig, or a combination of mIL-15/Ig and CTLA4/Ig.

An effective immune response begins when an antigen or mitogen triggers the activation of T cells. Antigenic fragments are presented in association with major histocompatibility complex (MHC) molecules on the surface of antigen presenting cells (APCs). APCs also deliver costimulatory signals, e.g., signals mediated by CD40/CD154 and CD28/B7-1 or B7-2 ("T-cell costimulation signals" or "costimulation signals"). In the process of T cell activation, numerous cellular changes occur, which include the expression of cytokines and cytokine receptors. One of the cytokines involved in the immune response is interleukin-15 (IL-15). IL-15 binds a heterotrimeric receptor consisting of β and γ subunits of other interleukin receptors and a unique IL-15Rα subunit. As described above, IL-15 has been characterized as a T cell growth factor that stimulates the proliferation and differentiation of B cells, T cells, natural killer (NK) cells, and lymphocyte-activated killer (LAK) cells in vitro. In vivo, the proliferation of these cell types enhances the immune response.

The present invention is based on the discovery of novel ways to inhibit the immune response. Inhibition can be achieved by administration of a combination of agents, one of which targets an IL-15R. The term "agent" is meant to encompass essentially any type of molecule that can be used as a therapeutic agent. Proteins, such as antibodies, fusion proteins, and soluble ligands, any of which may either be identical to a wild-type protein or contain a mutation (i.e., a deletion, addition, or substitution of one or more amino acid residues), and the nucleic acid molecules that encode them, are all "agents." The agents of the invention can be administered either systemically, or locally, or by way of cell-based therapies (i.e., an agent of the invention can be administered to a patient by administering a cell that expresses that agent to the patient). The cell can be a cell administered to the patient solely for the purpose of expressing the therapeutic agent. The cell can also be a cell of a cellular, organ or tissue transplant where the transplanted graft is treated with an agent or transduced with a nucleic acid encoding for a therapeutic agent prior to, ex vivo, or subsequent to, transplantation. In this way the transplanted cell produces its own immunosuppressive factor(s). For example, a cell with insulin production as a useful phenotype would modified to include a gene producing the immunosuppresive factor(s) of this invention. This and other methods of administration are routinely used by those of ordinary skill in the art and are discussed further below.

Agents that Target an IL-15R

Agents that target an IL-15R include agents that bind to an IL-15R as well as agents that bind to and subsequently destroy IL-15R-bearing cells, such as activated T cells. Thus, agents useful in achieving immune suppression can contain two functional moieties: a targeting moiety that targets the agent to an IL-15R-bearing cell and a target-cell depleting (e.g. lytic) moiety that leads to the elimination of the IL-15R-bearing cell. In one embodiment, the targeting moiety binds an IL-15R without effectively transducing a signal through that receptor. For example, the targeting moiety can include a mutant IL-15 polypeptide, and the target-cell depleting moiety can include the Fc region of an immunoglobulin molecule, where this Fc region is derived from an IgG, such as human IgG1, IgG2, IgG3, IgG4, or analogous mammalian IgGs or from an IgM, such as human IgM or analogous mammalian IgMs. In a preferred embodiment the Fc region includes the hinge, CH2 and CH3 domains of human IgG1 or murine IgG2a. Although the invention is not limited to agents that work by any particular mechanism, it is believed that the Fc region mediates complement and phagocyte-driven elimination of IL-15R-bearing cells.

Mutant IL-15 polypeptides that bind the IL-15 receptor complex with an affinity similar to wild-type IL-15, but fail to fully activate signal transduction, have been produced. These mutant polypeptides compete effectively with wild-type IL-15 polypeptides and can inhibit one or more of the events that normally occur in response to IL-15 signaling, such as cellular proliferation. The "wild-type IL-15 polypeptide" referred to herein is a polypeptide that is identical to a naturally occurring IL-15 (e.g., a wild-type IL-15 polypeptide is shown in FIG. 1). In contrast, a "mutant IL-15 polypeptide" is a polypeptide that has at least one mutation relative to wild-type IL-15 and that inhibits at least one of the in vivo or in vitro activity that is usually promoted by wild-type IL-15.

A mutant IL-15 polypeptide that can be used according to the present invention will generally block at least 40%, more preferably at least 70%, and most preferably at least 90% of one or more of the activities of the wild-type IL-15 molecule. The ability of a mutant IL-15 polypeptide to block wild-type IL-15 activity can be assessed by numerous assays, including the BAF-BO3 cell proliferation assay described herein (in which the cells were transfected with a construct encoding IL-2Rβ). Further, mutant polypeptides of the invention can be defined according the particular percent identity they exhibit with wild-type IL-15. When examining the percent identity between two polypeptides, the length of the sequences compared will generally be at least 16 amino acids, preferably at least 20 amino acids, more preferably at least 25 amino acids, and most preferably at least 35 amino acids. The term "identity," as used in reference to polypeptide or DNA sequences, refers to the identity between subunits (amino acid residues of proteins or nucleotides of DNA molecules) within the two polypeptide or DNA sequences being compared. When a subunit position in both of the molecules is occupied by the same monomeric subunit (i.e., the same amino acid residue or nucleotide), then the molecules are identical at that position. The similarity between two amino acid sequences or two nucleotide sequences is a direct function of the number of identical positions. Thus, a polypeptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria. Identity is typically and most conveniently measured using sequence analysis software, such as the Sequence Analysis Software Package of the Genetics Computer Group at the University of Wisconsin Biotechnology Center (1710 University Avenue, Madison, Wis. 53705), with the default parameters thereof.

A mutant IL-15 polypeptide can be at least 65%, preferably at least 80%, more preferably at least 90%, and most preferably at least 95% (e.g., 96%, 97%, 98% or 99%) identical to wild-type IL-15. The mutation can consist of a change in the number or content of amino acid residues. For example, the mutant IL-15 can have a greater or a lesser number of amino acid residues than wild-type IL-15. Alternatively, or in addition, the mutant polypeptide can contain a substitution of one or more amino acid residues that are present in the wild-type IL-15. The mutant IL-15 polypeptide can differ from wild-type IL-15 by the addition, deletion, or substitution of a single amino acid residue, for example, an addition, deletion or substitution of the residue at position 156. Similarly, the mutant polypeptide can differ from wild-type by an addition, deletion, or substitution of two amino acid residues, for example, the residues at positions 156 and 149. For example, the mutant IL-15 polypeptide can differ from wild-type IL-15 by the substitution of aspartate for glutamine at residues 156 and 149 (as shown in FIG. 2). Mutant polypeptides useful as targeting agents, like wild-type IL-15, recognize and bind a component of the IL-15R. In one embodiment, the mutation of IL-15 is in the carboxy-terminal domain of the cytokine, which is believed to bind IL-2Rγ (the IL-2 receptor subunit). Alternatively, or in addition, mutant IL-15 polypeptides can include one or more mutations within IL-2Rβ (the IL-2 receptor β subunit) binding domain.

In the event a mutant IL-15 polypeptide contains a substitution of one amino acid residue for another, the substitution can be, but is not necessarily, a conservative substitution, which includes a substitution within the following groups: glycine, alanine; valine, isoleucine, leucine; aspartic acid, glutamic acid; asparagine, glutamine; serine, threonine; lysine, arginine; and phenylalanine, tyrosine.

Instead of using, or in addition to using, an IL-15R polypeptide (e.g., a mutant IL-15 polypeptide), the IL-15R can be targeted with antibodies that bind a component of the IL-15R (e.g., the IL-15Rα subunit). The methods by which antibodies, including humanized antibodies, can be generated against a component of the IL-15R are well known in the art. The antibodies preferably should be able to activate complement and phagocytosis, e.g., human IgG3 and IgG1 (preferably the latter) subclasses, or murine IgG2a subclass.

As described above, agents useful in achieving immune suppression can contain two functional moieties: a targeting moiety that targets the agent to an IL-15R-bearing cell (such as the mutant IL-15 molecule just described) and a target-cell depleting moiety that, e.g., lyses or otherwise leads to the elimination of, the IL-15R-bearing cell. Thus, the agent can be a chimeric polypeptide that includes a mutant IL-15 polypeptide and a heterologous polypeptide such as the Fc region of the IgG and IgM subclasses of antibodies. The Fc region may include a mutation that inhibits complement fixation and Fc receptor binding, or it may be target-cell depleting (i.e., able to destroy cells by binding complement or by another mechanism, such as antibody-dependent complement lysis).

The Fc region can be isolated from a naturally occurring source, recombinantly produced, or synthesized (just as any polypeptide featured in the present invention can be). For example, an Fc region that is homologous to the IgG C-terminal domain can be produced by digestion of IgG with papain. IgG Fc has a molecular weight of approximately 50 kDa. The polypeptides of the invention can include the entire Fc region, or a smaller portion that retains the ability to lyse cells. In addition, full-length or fragmented Fc regions can be variants of the wild-type molecule. That is, they can contain mutations that may or may not affect the function of the polypeptide.

The Fc region can be "target-cell depleting" or "non-target-cell depleting." A non-target-cell depleting Fc region typically lacks a high affinity Fc receptor binding site and a C'1q binding site. The high affinity Fc receptor binding site of murine IgG Fc includes the Leu residue at position 235 of IgG Fc. Thus, the murine Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a target-cell depleting IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Target-cell depleting IgG Fc has wild-type residues or conservative amino acid substitutions at these sites. Target-cell depleting IgG Fc can target cells for antibody dependent cellular cytotoxicity or complement directed cytolysis (CDC). Appropriate mutations for human IgG are also known (see, e.g., Morrison et al., *The Immunologist* 2:119-124, 1994; and Brekke et al., *The Immunologist* 2:125, 1994).

Agents that target the IL-15R can also be agents that include a mutant IL-15 polypeptide and a polypeptide that functions as an antigenic tag, such as a FLAG sequence. FLAG sequences are recognized by biotinylated, highly specific, anti-FLAG antibodies, as described herein (see also Blanar et al., *Science* 256:1014, 1992; LeClair et al., *Proc. Natl. Acad. Sci.* USA 89:8145, 1992).

Agents that Inhibit a Costimulatory Signal

To inhibit an immune response, the agents that target IL-15R-bearing cells, described above, can be administered with an agent that inhibits a costimulatory signal that is normally transmitted from an APC to a T cell. An agent that is administered "with" another may be, but is not necessarily, administered at the same time. For example, in the context of the present invention, an agent that targets an IL-15R may be administered before or after an agent that inhibits a costimulatory signal. To inhibit a costimulatory signal, one can administer any agent that binds to and blocks one or more of the molecules, on either the T cell or the APC, that are known to participate in costimulatory signaling between those two cell types. For example, one can administer any agent that binds to a B7 molecule (including, but not limited to, B7-1 or B7-2) on an APC or to CD28, which is expressed e.g. by T cells and bound by B7. These agents include antibodies that bind B7 molecules (e.g., an anti-B7 antibody), CTLA4/Ig, and antibodies that bind CD28. Alternatively, or in addition, one can administer any agent that binds CD40 on an APC or CD40L (also known as CD154), which is expressed e.g. by T cells and bound by CD40. These agents include antibodies that bind CD40 or CD40L.

Procedures for Screening Agents that Inhibit the Immune Response

In addition to testing a candidate agent (e.g., a mutant IL-15 polypeptide) in the in vitro assays described in the examples below, one can use any of the following in vivo assays to test which particular combinations of the agents described herein most effectively bring about immune suppression. For example, one can test one or more of the agents that target the IL-15R in combination with one or more of the agents that either block the costimulatory signal that is normally transmitted from APCs to T cells, antagonize the TCR, inhibit calcineurin, inhibit cellular proliferation, or that bind to and inactivate antigen-activated T cells. These in vivo assays represent only some of the routine ways in which one of ordinary skill in the art could further test the efficacy of agents of the invention. They were selected for inclusion here because of their relevance to the variety of clinical conditions amenable to treatment with agents that target the IL-15R. For example, the assays are relevant to organ transplantation, immune disease, particularly autoimmune disease, and cancers of the immune system (e.g. cancers that arise when T cells become malignant).

Transplantation Paradigms

To determine whether an agent of the invention, or a combination of such agents, achieves immune suppression, they can be administered (either directly, by gene-based therapy, or by cell-based therapy) in the context of well-established transplantation paradigms.

Agents of the invention, or nucleic acid molecules encoding them, can be systemically or locally administered by standard means to any conventional laboratory animal, such as a rat, mouse, rabbit, guinea pig, or dog, before an allogeneic or xenogeneic skin graft, organ transplant, or cell implantation is performed on the animal. Strains of mice such as C57B1-10, B10.BR, and B10.AKM (Jackson Laboratory, Bar Harbor, Me.), which have the same genetic background but are mismatched for the H-2 locus, are well suited for assessing various organ grafts.

Heart Transplantation

A method for performing cardiac grafts by anastomosis of the donor heart to the great vessels in the abdomen of the host was first published by Ono et al. (*J. Thorac. Cardiovasc. Surg.* 57:225, 1969; see also Corry et al., *Transplantation* 16:343, 1973). By way of this surgical procedure, the aorta of a donor heart is anastomosed to the abdominal aorta of the host, and the pulmonary artery of the donor heart is anastomosed to the adjacent vena cava using standard microvascular techniques. Once the heart is grafted in place and warmed to 37° C. with Ringer's lactate solution, normal sinus rhythm will resume. Function of the transplanted heart can be assessed frequently by palpation of ventricular contractions through the abdominal wall. Rejection is defined as the cessation of myocardial contractions. Agents of the invention (e.g., a combination of mutant IL-15/Fc and CTLA4/Ig) would be considered effective in reducing organ rejection if hosts that received these agents experienced a longer period of engraftment of the donor heart than did untreated hosts.

Skin Grafting

The effectiveness of various combinations of the agents of the invention can also be assessed following a skin graft. To perform skin grafts on a rodent, a donor animal is anesthetized and the full thickness skin is removed from a part of the tail. The recipient animal is also anesthetized, and a graft bed is prepared by removing a patch of skin from the shaved flank. Generally, the patch is approximately 0.5×0.5 cm. The skin from the donor is shaped to fit the graft bed, positioned, covered with gauze, and bandaged. The grafts can be inspected daily beginning on the sixth post-operative day, and are considered rejected when more than half of the transplanted epithelium appears to be non-viable. Agents of the invention (e.g., a combination of mutant IL-15/Fc and CTLA4/Ig) would be considered effective in reducing skin graft rejection if hosts that received these agents experienced a longer period of engraftment of the donor skin than did untreated hosts.

Islet Allograft Model

DBA/2J islet cell allografts can be transplanted into rodents, such as 6-8 week-old B6 AF1 mice rendered diabetic by a single intraperitoneal injection of streptozotocin (225 mg/kg; Sigma Chemical Co., St. Louis, Mo.). As a control, syngeneic islet cell grafts can be transplanted into diabetic mice. Islet cell transplantation can be performed by following published protocols (for example, see Gotoh et al., *Transplantation* 42:387, 1986). Briefly, donor pancreata are perfused in situ with type IV collagenase (2 mg/ml; Worthington Biochemical Corp., Freehold, N.J.). After a 40-minute digestion period at 37° C., the islets are isolated on a discontinuous Ficoll gradient. Subsequently, 300-400 islets are transplanted under the renal capsule of each recipient. Allograft function can be followed by serial blood glucose measurements (Accu-Check III™; Boehringer, Mannheim, Germany). Primary graft function is defined as a blood glucose level under 11.1 mmol/l on day 3 post-transplantation, and graft rejection is defined as a rise in blood glucose exceeding 16.5 mmol/l (on each of at least 2 successive days) following a period of primary graft function.

Models of Autoimmune Disease

Models of autoimmune disease provide another means to assess combinations of the agents of the invention in vivo. These models are well known to those of ordinary skill in the art and can be used to determine whether a given combination of agents, which includes an agent that targets an IL-15R, would be therapeutically useful in treating a specific autoimmune disease when delivered either directly, via genetic therapy, or via cell-based therapies.

Autoimmune diseases that have been modeled in animals include rheumatic diseases, such as rheumatoid arthritis and systemic lupus erythematosus (SLE), type I diabetes, and autoimmune diseases of the thyroid, gut, and central nervous system. For example, animal models of SLE include MRL mice, BXSB mice, and NZB mice and their $F_1$ hybrids. These animals can be crossed in order to study particular aspects of the rheumatic disease process; progeny of the NZB strain develop severe lupus glomerulonephritis when crossed with NZW mice (Bielschowsky et al., *Proc. Univ. Otago Med. Sch.* 37:9, 1959; see also *Fundamental Immunology*, Paul, Ed., Raven Press, New York, N.Y., 1989). Similarly, a shift to lethal nephritis is seen in the progeny of NBZ×SWR matings (Data et al., *Nature* 263:412, 1976). The histological appearance of renal lesions in $SNF_1$ mice has been well characterized (Eastcott et al., *J. Immunol.* 131:2232, 1983; see also *Fundamental Immunology*, supra). Therefore, the general health of the animal as well as the histological appearance of renal tissue can be used to determine whether the administration of agents that target an IL-15R and, e.g., inhibit costimulation, can effectively suppress the immune response in an animal model of SLE.

One of the MRL strains of mice that develops SLE, MRL-lpr/lpr, also develops a form of arthritis that resembles rheumatoid arthritis in humans (Theofilopoulos et al., *Adv. Immunol.* 37:269, 1985). Alternatively, an experimental arthritis can be induced in rodents by injecting rat type II collagen (2 mg/ml) mixed 1:1 in Freund's complete adjuvant (100 μl total) into the base of the tail. Arthritis develops 2-3 weeks after immunization. The ability of nucleic acid molecules encoding agents of the invention (e.g., agents that target the IL-15R and agents that inhibit costimulation or that bind to and inactivate antigen-activated T cells) to suppress an immune response can be assessed by targeting the nucleic acid molecules to T lymphocytes. One way to target T lymphocytes is as follows. Spleen cell suspensions are prepared 2-3 days after the onset of arthritis and incubated with collagen (100 μg/ml) for 48 hours to induce proliferation of collagen-activated T cells. During this time, the cells are transduced with a vector encoding the polypeptide agent of interest. As a control, parallel cultures are grown but not transduced or, transduced with an "empty" vector. The cells are then injected intraperitoneally ($5 \times 10^7$ cells/animal). The effectiveness of the treatment is assessed by following the disease symptoms during the subsequent 2 weeks, as described by Chernajovsky et al. (*Gene Therapy* 2:731-735, 1995). Lesser symptoms, compared to control, indicate that the combined agents of the invention, and the nucleic acid molecules that encode them, function as immunosuppressants and are therefore useful in the treatment of immune disease, particularly autoimmune disease.

The ability of various combinations of agents to suppress the immune response in the case of Type I diabetes can be tested in the BB rat strain, which was developed from a commercial colony of Wistar rats at the Bio-Breeding Laboratories in Ottawa. These rats spontaneously develop autoantibodies against islet cells and insulin, just as occurs with human Type I diabetes. Alternatively, NOD (non-obese diabetic) mice can be used as a model system.

Autoimmune diseases of the thyroid have been modeled in the chicken. Obese strain (OS) chickens consistently develop spontaneous autoimmune thyroiditis resembling Hashimoto's disease (Cole et al., *Science* 160:1357, 1968). Approximately 15% of these birds produce autoantibodies to parietal cells of the stomach, just as in the human counterpart of autoimmune thyroiditis. The manifestations of the disease in OS chickens, which could be monitored in the course of any treatment regime, include body size, fat deposit, serum lipids, cold sensitivity, and infertility.

Models of autoimmune disease in the central nervous system (CNS) can also be experimentally induced. An inflammation of the CNS, which leads to paralysis, can be induced by a single injection of brain or spinal cord tissue with adjuvant in many different laboratory animals, including rodents and primates. This model, referred to as experimental allergic encephalomyelitis (EAE) is T cell mediated. Similarly, experimentally induced myasthenia gravis can be produced by a single injection of acetylcholine receptor with adjuvants (Lennon et al., *Ann. N.Y. Acad. Sci.* 274:283, 1976).

Autoimmune diseases of the gut can be modeled in IL-2 or IL-10 "knock out" mice, or in mice that receive enemas containing bovine serum albumin.

Nucleic Acid Molecules that Encode Agents of the Invention

Polypeptide agents of the invention, including those that are fusion proteins (e.g., the mutant IL-15/Fc and CTLA4/Ig molecules) can not only be obtained by expression of a nucleic acid molecule in a suitable eukaryotic or prokaryotic expression system in vitro and subsequent purification of the polypeptide agent, but can also be administered to a patient by way of a suitable gene therapeutic expression vector encoding a nucleic acid molecule. Further more a nucleic acid can be introduced into a cell of a graft prior to transplantation of the graft. Thus, nucleic acid molecules encoding the agents described above are within the scope of the invention. Just as polypeptides of the invention (e.g., mutant IL-15/Fc polypeptides) can be described in terms of their identity with wild-type polypeptides (e.g. wild-type IL-15 polypeptides), the nucleic acid molecules encoding them will necessarily have a certain identity with those that encode the corresponding wild-type polypeptides. For example, the nucleic acid molecule encoding a mutant IL-15 polypeptide can be at least 65%, preferably at least 75%, more preferably at least 85%, and most preferably at least 95% (e.g., 96%, 97%, 98%, or 99%) identical to the nucleic acid encoding wild-type IL-15. For nucleic acids, the length of the sequences compared will generally be at least 50 nucleotides, preferably at least 60 nucleotides, more preferably at least 75 nucleotides, and most preferably 110 nucleotides.

The nucleic acid molecules that encode agents of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules of the invention are referred to as "isolated" because they are separated from either the 5' or the 3' coding sequence with which they are immediately contiguous in the naturally occurring genome of an organism. Thus, the nucleic acid molecules are not limited to sequences that encode polypeptides; some or all of the non-coding sequences that lie upstream or downstream from a coding sequence can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced by in vitro transcription.

The isolated nucleic acid molecules of the invention can include fragments not found as such in the natural state. Thus, the invention encompasses recombinant molecules, such as those in which a nucleic acid sequence (for example, a sequence encoding a mutant IL-15) is incorporated into a vector (for example, a plasmid or viral vector) or into the genome of a heterologous cell (or the genome of a homologous cell, at a position other than the natural chromosomal location).

As described above, agents of the invention can be fusion proteins. In addition to, or in place of, the heterologous polypeptides described above, a nucleic acid molecule encoding an agent of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-β-phosphotransferase (HPH), thymidine kinase (TK), lacZ (encoding β-galactosidase), and xanthine guanine phosphoribosyltransferase (XGPRT). As with many of the standard procedures associated with the practice of the invention, one of ordinary skill in the art will be aware of additional useful reagents, for example, of additional sequences that can serve the function of a marker or reporter.

The nucleic acid molecules of the invention can be obtained by introducing a mutation into an agent of the invention (e.g., an IL-15 molecule or a CTLA4 molecule) obtained from any biological cell, such as the cell of a mammal, or produced by routine cloning methods. Thus, the nucleic acids of the invention can be those of a mouse, rat, guinea pig, cow, sheep, horse, pig, rabbit, monkey, baboon, dog, or cat. Preferably, the nucleic acid molecules will be those of a human.

The nucleic acid molecules described above can be contained within a vector that is capable of directing their expression in, for example, a cell that has been transduced with the vector. Accordingly, in addition to polypeptide agents, expression vectors containing a nucleic acid molecule encoding those agents and cells transfected with those vectors are among the preferred embodiments.

Vectors suitable for use in the present invention include T7-based vectors for use in bacteria (see, e.g., Rosenberg et al., *Gene* 56:125, 1987), the pMSXND expression vector for use in mammalian cells (Lee and Nathans, *J. Biol. Chem.* 263:3521, 1988), yeast expression systems, such as *Pichia pastoris* (for example the PICZ family of expression vectors from Invitrogen, Carlsbad, Calif.) and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionine promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. One of ordinary skill in the art is well aware of numerous promoters and other regulatory elements that can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Other feasible selectable marker genes allowing for phenotypic selection of cells include various fluorescent proteins, e.g. green fluorescent protein (GFP) and variants thereof. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, e.g., Gluzman (Ed.), *Eukaryotic Viral Vectors*, CSH Laboratory Press, Cold Spring Harbor, N.Y.).

Prokaryotic or eukaryotic cells that contain a nucleic acid molecule that encodes an agent of the invention and express the protein encoded in that nucleic acid molecule in vitro are also features of the invention. A cell of the invention is a transfected cell, i.e., a cell into which a nucleic acid molecule, for example a nucleic acid molecule encoding a mutant IL-15 polypeptide, has been introduced by means of recombinant DNA techniques. The progeny of such a cell are also considered within the scope of the invention. The precise components of the expression system are not critical. For example, a mutant IL-15 polypeptide can be produced in a prokaryotic host, such as the bacterium *E. coli*, or in a eukaryotic host, such as an insect cell (for example, Sf21 cells), or mammalian cells (e.g., COS cells, CHO cells, 293 cells, NIH 3T3 cells, or HeLa cells). These cells are available from many sources, including the American Type Culture Collection (Manassas, Va.). In selecting an expression system, it matters only that the components are compatible with one another. One of ordinary skill in the art is able to make such a determination. Furthermore, if guidance is required in selecting an expression system, one can consult Ausubel et al. (*Current Protocols in Molecular Biology*, John Wiley and Sons, New York, N.Y., 1993) and Pouwels et al. (*Cloning Vectors: A Laboratory Manual*, 1985 Suppl. 1987).

Eukaryotic cells that contain a nucleic acid molecule that encodes the agent of the invention and express the protein encoded in such nucleic acid molecule in vivo are also features of the invention.

Furthermore, eukaryotic cells of the invention can be cells that are part of a cellular transplant, a tissue or organ transplant. Such transplants can comprise either primary cells taken from a donor organism or cells that were cultured, modified and/or selected in vitro before transplantation to a recipient organism, e.g. eukaryotic cells lines, including stem cells or progenitor cells. Since, after transplantation into a recipient organism, cellular proliferation may occur, the progeny of such a cell are also considered within the scope of the invention. A cell, being part of a cellular, tissue or organ transplant, can be transfected with a nucleic acid encoding a mutant 11-15 polypeptide and subsequently be transplanted into the recipient organism, where expression of the mutant IL-15 polypeptide occurs. Furthermore, such a cell can contain one or more additional nucleic acid constructs allowing for application of selection procedures, e.g. of specific cell lineages or cell types prior to transplantation into a recipient organism.

The expressed polypeptides can be purified from the expression system using routine biochemical procedures, and can be used as diagnostic tools or as therapeutic agents, as described below (the therapeutic compositions of the invention can be understood as pharmaceuticals). Accordingly, the invention also features a method of making a therapeutic composition comprising a mutant IL-15 polypeptide that binds a subunit of an IL-15R and a polypeptide that binds a B7 molecule. The method can be carried out, for example, by (a) purifying the mutant IL-15 polypeptide from an expression system; (b) purifying the polypeptide that binds B7 from an expression system; and (c) combining the IL-15 polypeptide and the polypeptide that binds B7. The therapeutic composition can be formulated (as described herein, and by methods known to those of ordinary skill in the art) to treat patients having any of the immune diseases (e.g. any of the autoimmune diseases) described herein).

Agents that Target an IL-15R are Useful in Making Diagnoses

Agents that target an IL-15R can be used to determine whether a patient has a disease (e.g., an immune disease, particularly autoimmune disease) that is amenable to treatment with a combination of the agents described herein. The diagnostic method can be carried out, for example, by obtaining a sample of tissue from a patient suspected of having an immune disease, particularly autoimmune disease or a cancer that is manifest as malignant immune cells and exposing that tissue to an antigenically-tagged polypeptide that targets an IL-15R. The sample may be any biological sample, such as a blood, urine, serum, or plasma sample. In addition, the sample may be a tissue sample (e.g., biopsy tissue), or an effusion obtained from a joint (e.g., synovial fluid), from the abdominal cavity (e.g., ascites fluid), from the chest (e.g., pleural fluid), or from the central nervous system (e.g., cerebral spinal fluid). The sample may also consist of cultured cells that were originally obtained from a patient (e.g., peripheral blood mononuclear cells). The sample can be obtained from a mammal, such as a human patient. If the sample contains cells that are bound by the agent to which they are exposed, it is highly likely that they would be bound by that agent (e.g. an agent that targets an IL-15R) in vivo and could thereby be inhibited from proliferating or destroyed in vivo. The presenting symptoms of candidate patients for such testing and the relevant tissues to be sampled given a particular set of symptoms are well known to one of ordinary skill in the art.

Patients Amenable to Treatment

Combinations of the agents of the invention can be used to treat patients who are suffering from an immune disease, particularly an autoimmune disease, including but not limited to the following: (1) a rheumatic disease such as rheumatoid arthritis, systemic lupus erythematosus, Sjögren's syndrome, scleroderma, mixed connective tissue disease, dermatomyositis, polymyositis, Reiter's syndrome or Behcet's disease (2) type I or type II diabetes (3) an autoimmune disease of the thyroid, such as Hashimoto's thyroiditis or Graves' Disease (4) an autoimmune disease of the central nervous system, such as multiple sclerosis, myasthenia gravis, or encephalomyelitis (5) a variety of phemphigus, such as phemphigus vulgaris, phemphigus vegetans, phemphigus foliaceus, Senear-Usher syndrome, or Brazilian phemphigus, (6) diseases of the skin such as psoriasis or neurodermitis, and (7) inflammatory bowel disease (e.g., ulcerative colitis or Crohn's Disease). Combinations of the agents of the invention can also be used to treat acquired immune deficiency syndrome (AIDS). Similarly, methods by which these agents are administered can be used to treat a patient who has received a transplant of synthetic or biological material, or a combination of both. Such transplants can be organ, tissue or cell transplants, or synthetic grafts seeded with cells, e.g. synthetic vascular grafts seeded with vascular cells. In addition, patients who have received a vascular injury would benefit from this method.

Because the invention encompasses administration of a target-cell depleting form of an agent that targets the IL-15R, it is possible to selectively kill autoreactive or "transplant destructive" immune cells without massive destruction of normal T cells. Accordingly, the invention features a method of killing cells that express the IL-15R in vivo, which includes activated or autoreactive or "transplant destructive" immune cells or malignant cells. These methods can be carried out by administering to a patient a combination of agents that includes an agent that targets the IL-15R and that activates the complement system, lyses cells by the ADCC mechanism, or otherwise kill cells expressing the wild-type IL-15 receptor complex. This method can be used to treat patients who have IL-15R$^+$ leukemia, lymphoma, or other IL-15R$^+$ malignant diseases, such as colon cancer.

Formulations for Use and Routes of Administration

The methods of the present invention and the therapeutic compositions used to carry them out contain "substantially pure" agents. For example, in the event the agent is a polypeptide, the polypeptide is at least 60% by weight (dry weight) the polypeptide of interest, e.g., a polypeptide that binds and destroys IL-15R-bearing cells. Preferably, the agents (e.g., the polypeptides) are at least 75%, more preferably at least 90%, and most preferably at least 99%, by weight, the agent of interest. Purity can be measured by any appropriate standard method, e.g., column chromatography, polyacrylamide gel electrophoresis, or HPLC analysis.

Although agents useful in the methods of the present invention can be obtained from naturally occurring sources, they can also be synthesized or otherwise manufactured (e.g., agents that bind and destroy IL-15R-bearing cells can be produced by expression of a recombinant nucleic acid molecule). Polypeptides that are derived from eukaryotic organisms or synthesized in *E. coli*, or other prokaryotes, and polypeptides that are chemically synthesized will be substantially free from their naturally associated components. In the event the polypeptide is a chimera, it can be encoded by a hybrid nucleic acid molecule containing one sequence that encodes all or part of the agent (e.g., a sequence encoding a mutant IL-15 polypeptide and sequence encoding an Fc region of IgG). Agents of the invention (e.g., polypeptides) can be fused to a hexa-histidine tag to facilitate purification of bacterially expressed protein, or to a hemagglutinin tag to facilitate purification of protein expressed in eukaryotic cells.

The techniques that are required to make the agents of the invention are routine in the art, and can be performed without resort to undue experimentation by one of ordinary skill in the art. For example, a mutation that consists of a substitution of one or more of the amino acid residues in IL-15 can be created using the PCR-assisted mutagenesis technique described herein for the creation of the mutant IL-15 polypeptide in which glutamine residues at positions 149 and 156 were changed to aspartic acid residues. Mutations that consist of deletions or additions of amino acid residues (to an IL-15 polypeptide or to any of the other useful polypeptides described herein, e.g., polypeptides that inhibit costimulation or that bind activated T cells) can also be made with standard recombinant techniques. In therapeutic applications, agents of the invention can be administered with a physiologically acceptable carrier, such as physiological saline. The therapeutic compositions of the invention can also contain a carrier or excipient, many of which are known to one of ordinary skill in the art. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol. The agents of the invention can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences."

Routes of administration are also well known to skilled pharmacologists and physicians and include intraperitoneal, intramuscular, subcutaneous, and intravenous administration. Additional routes include intracranial (e.g., intracisternal or intraventricular), intraorbital, ophthalmic, intracapsular, intraspinal, intraperitoneal, transmucosal, topical, subcutaneous, and oral administration. It is expected that the intravenous or intra-arterial routes will be preferred for the administration of agents that target an IL-15 receptor. The subcutaneous route may also be used frequently as the subcutaneous tissue provides a stable environment for polypeptides, from which they can be slowly released.

In case of cell-based therapies (gene therapies), the cells/tissues/organs could either be transfected by incubation, infusion or perfusion prior to transplantation with a nucleic acid composition, such that the therapeutic protein is expressed and subsequently released by the transplanted cells/tissues/organs within the recipient organism. As well, the cells/tissues/organs could undergo a pretreatment by perfusion or simple incubation with the therapeutic protein prior to transplantation in order to eliminate transplant-associated immune cells adherent to the donor cells/tissues/organs (although this is only a side aspect, which will probably not be of any clinical relevance). In the case of cell transplants, the cells may be administered either by an implantation procedure or with a catheter-mediated injection procedure through the blood vessel wall. In some cases, the cells may be administered by release into the vasculature, from which the subsequently are distributed by the blood stream and/or migrate into the surrounding tissue (this is done in islet cells transplantation, where the islet cells are released into the portal vein and subsequently migrate into liver tissue).

It is well known in the medical arts that dosages for any one patient depend on many factors, including the general health, sex, weight, body surface area, and age of the patient, as well as the particular compound to be administered, the time and route of administration, and other drugs being administered concurrently. Dosages for the polypeptide of the invention will vary, but can, when administered intravenously, be given in doses on the order of magnitude of 1 microgram to 10 mg/kg body weight or on the order of magnitude of 0.01 mg/l to 100 mg/l of blood volume. A dosage can be administered one or more times per day, if necessary, and treatment can be continued for prolonged periods of time. Determining the correct dosage for a given application is well within the abilities of one of ordinary skill in the art.

EXAMPLES

Reagents

The following reagents were used in the studies described herein: recombinant human IL-2 was obtained from Hoffman-La Roche (Nutley, N.J.); rapamycin was obtained from Wyeth-Ayerst (Princeton, N.J.); cyclosporine-A (CsA) was obtained from Sandoz (East Hanover, N.J.); RPMI-1640 and fetal calf serum (FCS) were obtained from BioWittaker (Walkersville, Md.); penicillin, streptomycin, G418, and strepavidin-RED670 were obtained from Gibco-BRL (Gaithersburg, Md.); dexamethasone, PHA, lysozyme, Nonidet P40, NaCl, HEPES, and PMSF were obtained from Sigma (St. Louis, Mo.); Ficoll-Hypaque was obtained from Pharmacia Biotech (Uppsala, Sweden); recombinant human IL-15 and anti-human IL-15 Ab were obtained from Pepro-Tech (Rocky Hill, N.J.); anti-FLAG Ab and anti-FLAG-affinity beads were obtained from International Biotechnologies, Inc. (Kodak, New Haven, Conn.); pRcCMV was obtained from InVitrogen Corporation (San Diego, Calif.); genistein was obtained from ICN Biomedicals (Irvine, Calif.); disuccinimidyl suberate (DSS) was obtained from Pierce (Rockford, Ill.); restriction endonucleases were obtained from New England Biolabs (Beverly, Mass.); [$^3$H] TdR was obtained from New England Nuclear (Boston, Mass.); and fluorescent dye conjugated antibodies CD25-PE[3], CD14-PE, CD16-PE, CD122-PE, CD4-FITC, CD8-FITC, IgG1-PE or IgG1-FITC were obtained from Beckton/Dickinson (San Jose, Calif.). FLAG peptide was synthesized in the Peptide Synthesis Facility at Harvard Medical School.

Production of FLAG-HMK-L-15 Fusion Protein

To study the cellular pattern of human IL-15 receptor expression, a plasmid that could be used to express an IL-15 fusion protein was constructed. The plasmid encodes an IL-15 polypeptide having an N-terminus covalently bound to the 18 amino acid FLAG-HMK-sequence (FLAG-HMK-IL-15). FLAG sequences are recognized by biotinylated, highly specific anti-FLAG antibodies (Blanar et al., *Science* 256:1014, 1992); LeClair et al., *Proc. Natl. Acad. Sci.* USA 89:8145, 1992) while HMK (Heart Muscle Kinase recognition site) sequences allow introduction of radioactive label [$^{32}$P] into the molecule (Blanar et al., supra, LeClair et al., supra).

For the construction of the plasmid FLAG-HMK-IL-15, a 322 bp cDNA fragment encoding mature IL-15 protein was amplified by PCR utilizing synthetic oligonucleotides [sense 5'-GG<u>AATTC</u>AACTGGGTGAATGTAATA-3' (SEQ ID NO:5; EcoRI site (underlined) plus bases 145-162); antisense 5'-CG<u>GGATCC</u>TCAAGAAGTGTTGATGAA-3' (SEQ ID NO:6; BamHI site [underlined] plus bases 472-489)]. The template DNA was obtained from PHA-activated human PBMCs. The PCR product was purified, digested with EcoRI and BamHI, and cloned into the pAR(DRI)59/60 plasmid digested with EcoRI-BamHI as described (Blanar et al., *Science* 256:1014, 1992; LeClair et al., *Proc. Natl. Acad. Sci.* USA 89:8145, 1992). The backbone of the pAR(DRI)59/60 plasmid contains in frame sequences encoding the FLAG and HMK recognition peptide sequences (Blanar et al, *Science* 256:1014, 1992; LeClair et al., *Proc. Natl. Acad. Sci.* USA 89:8145, 1992).

Expression and Purification of FLAG-HMK-IL-15 Fusion Protein

The IL-15-related fusion construct, FLAG-HMK-IL-15, was expressed in BL-21 strain *E. coli* and affinity purified with anti-FLAG coated beads as described (Blanar et al., *Science* 256:1014, 1992; LeClair et al., *Proc. Natl. Acad. Sci.* USA 89:8145, 1992). The fusion protein was eluted from affinity columns after extensive washing with 0.1 M glycine (pH 3.0). The eluate containing FLAG-HMK-IL-15 was dialyzed against a buffer containing 50 mM Tris (pH 7.4) and 0.1 M NaCl for 18 hours at 4° C., filtered through a 0.2 μm membrane, and stored at −20° C.

FLAG-HMK-IL-15 Binds the IL-15Rα Subunit

The purified FLAG-HMK-IL-15 fusion protein was tested to determine whether it interacts with cell surface IL-15 receptors. As described above, [$^{32}$P]-FLAG-HMK-IL-15 was added to cultures of PBMCs that were activated by a mitogen, PHA. In order to permanently bind interactive proteins to one another, the chemical cross-linker disuccinimidyl suberate (DSS) was added. The cells were washed, lysed, centrifuged, and detergent-soluble proteins were separated by SDS-PAGE. Autoradiography of SDS-PAGE separated proteins revealed a single 75-80 kDa band corresponding to the combined molecular weight of FLAG-HMK-IL-15 (15 kDa) and the human IL-15Rα subunit (60-65 kDa). The identity of this band as the IL-15Rα subunit was confirmed by cross-linking experiments conducted in the presence of a molar excess of mIL-15. Under these conditions, we failed to detect the radiolabeled 15 kDa band. Thus, the conformation of [$^{32}$P]-FLAG-HMK-IL-15 fusion proteins allows site specific binding to the 60-65 kDa IL-15Rα subunit expressed on the surface of mitogen-activated PBMCs.

FLAG-HMK-IL-15 is a Biologically Active Growth Factor that Requires Expression of IL-2Rβ

In the next series of experiments, the FLAG-HMK-IL-15 fusion protein was tested to determine whether it could function as a biologically active growth factor. PHA-activated human PBMCs proliferate in response to either FLAG-HMK-IL-15 or human recombinant IL-2, as detected via the [$^3$H]-TdR incorporation assay. A FLAG peptide lacking the IL-15 sequence does not stimulate cell proliferation. As does IL-2, the FLAG-HMK-IL-15 fusion protein stimulates proliferation of IL-2Rγ$^+$BAF-BO3 cell transfectants that express the IL-2Rβ subunit. The FLAG-HMK-IL-15 fusion protein does not, however, stimulate the proliferation of parental BAF-BO3 cells that were transfected with a vector lacking IL-2Rβ chain sequences. Thus, FLAG-HMK-IL-15 is a biologically active growth factor that requires expression of IL-2Rβ chains upon target cells in order to stimulate cellular proliferation.

Mitogen-Activated, but not Resting, PBMCs Express the IL-15Rα Subunit

The FLAG-HMK-IL-15 fusion protein, biotinylated anti-FLAG antibody, and streptavidin-RED670 were employed to detect expression of IL-15 binding sites on human PBMCs by cytofluorometric analysis. The PBMCs tested were either freshly isolated or PHA-activated. These cells were washed and incubated with either medium alone or FLAG-HMK-IL-15 followed by anti-FLAG biotinylated Ab and streptavidin-RED670. The stained cells were analyzed by flow cytometry. PBMCs that were activated with PHA expressed IL-15Rα proteins but resting PBMCs did not. In keeping with the result of the cross-linking experiments described above, binding of FLAG-HMK-IL-15 to PHA activated PBMCs is blocked by a molar excess of mIL-15, thereby demonstrating the specificity of FLAG-HMK-IL-15 binding for IL-15 binding sites. Both activated CD4$^+$ and CD8$^+$ cells express IL-15α chains. Activation induced IL-15Rα chains were also detected on CD14+(monocyte/macrophage) cells and CD16$^+$ (natural killer) cells.

IL-2Rα and IL-2Rβ Subunits are not Required for IL-15 Binding

FACS analysis of PHA-activated PBMCs stained with FLAG-HMK-IL-15 proteins and anti-CD25 Mab, against the IL-2Rα subunit, reveals cell populations expressing both IL-15Rα and IL-2Rα subunits, as well as cell populations that express either subunit, but not both. There are IL-2Rα$^+$ cells that do not bind FLAG-HMK-IL-15. Almost all PBMCs that were stimulated with PHA for only one day express either IL-15Rα or IL-2Rβ chains, but not both proteins. In contrast, 3 days following PHA stimulation, a far larger population of IL-15Rα+, IL-2Rβ+ cells (double positive) and a far smaller population of IL-15Rα+, IL-cells (single positive) were noted. Interestingly, there are IL-2Rβ+ cells that fail to bind IL-15. Therefore, expression of IL-2Rβ chains is not sufficient for IL-15 binding.

Taken together, these data indicate that IL-15 can bind IL-15Rα+, IL-2Rα−, and IL-2Rβ− cells. A similar conclusion was reached through experimentation that probed the interaction of IL-15 with IL-2Rα−, β− cells transfected with IL-15Rα subunit (Anderson et al., *J. Biol. Chem.* 270:29862, 1995; Giri et al., *EMBO J.* 14:3654, 1995). In addition to the requirement for IL-15Rα subunit expression, the IL-2Rβ and IL-2Rγ subunits are required to render cells sensitive to IL-15 triggered growth.

In summary, the experiments presented above have demonstrated that: (i) IL-15Rα subunits are rapidly expressed by activated macrophages, T cells, and NK cells, and (ii) induction of the IL-15Rα subunit is blocked by dexamethasone but not by CsA or rapamycin. In addition, the experiments have confirmed that the IL-15Rα subunit is necessary and sufficient for IL-15 binding and that the FLAG-HMK-IL-15 fusion protein is an extremely useful tool for studying IL-15 receptors.

The Pattern of Tyrosine Phosphorylated Proteins Induced by IL-2 is the Same as that Induced by IL-15.

The IL-2Rβ Subunit is Critical for both IL-2 and IL-15 Signal Transduction

Decreasing the viability of activated T cells and thereby depleting activated T cells provides a way to decrease the production of lymphokines and mitogens that contribute to accelerated atherosclerosis, allograft rejection, certain leukemias and other immune-mediated pathologies. In addition, blocking the signal transduction pathway activated by IL-15 also provides a way to decrease the production of lymphokines and mitogens that contribute to accelerated atherosclerosis, allograft rejection, certain leukemias and other immune-mediated pathologies. When activated, T cells proliferate and express receptors on their cell surface for interleukins. In addition, activated T cells release at least 3 lymphokines: gamma interferon, B cell differentiation factor II, and IL-3. These lymphokines can produce various undesirable events, such as allograft rejection. In contrast, resting T cells and long-term memory T cells do not express lymphokine receptors. This difference in receptor expression provides a means to target activated immune cells without interfering with resting cells. Molecules designed to recognize some subunit of the IL-15R will recognize activated monocytes/macrophages as well as activated T cells and can be used to selectively inhibit or destroy these cells. Derivatives of IL-15 that bind to an IL-15R subunit but that lack IL-15 activity, either because they block the binding and/or uptake of bona fide IL-15, are useful in the method of the invention. The mutant IL-15 molecule described below provides a working example of such a derivative.

A Mutant IL-15 Polypeptide that Targets an IL-15R
Genetic Construction of Mutant IL-15

The human IL-15 protein bearing a double mutation (Q149D; Q156D) was designed to target the putative sites critical for binding to the IL-2Rγ subunit. The polar, but uncharged glutamine residues at positions 149 and 156 were mutated into acidic residues of aspartic acid utilizing PCR-assisted mutagenesis. A cDNA encoding the double mutant of IL-15 was amplified by PCR utilizing a synthetic sense oligonucleotide [5'-G GAATTCAACTGGGTGAATGTAATA-3' (SEQ ID NO:5); EcoRI site (underlined hexamer) plus bases 145-162] and a synthetic antisense oligonucleotide (5'-CG GGATCCTCAAGAAGTGTTGATGAACATGT CGACAATATGTACAAAACTGTCCAAAAAT-3' (SEQ ID NO:7); BamHI site (underlined hexamer) plus bases 438-489; mutated bases are singly underlined]. The template was a plasmid containing cDNA that encodes human FLAG-HMK-IL-15. The amplified fragment was digested with EcoRI/BamHI and cloned into the pAR(DRI)59/60 plasmid digested with EcoRI/BamRI as described (LeClair et al., *Proc. Natl. Acad. Sci.* USA 89:8145, 1989). The presence of a mutation at residue 156 was confirmed by digestion with SalI; the mutation introduces a new SalI restriction site. In addition, mutations were verified by DNA sequencing, according to standard techniques. The FLAG-HMK-IL-15 (Q149D; Q156D) double mutant protein was produced, purified, and verified by sequencing as described above for the FLAG-HMK-IL-15 wild-type protein.

Using this same strategy, mutants that contain a single amino acid substitution, either at position 149 or at position 156 were prepared. As described above, these positions (149 and 156) correspond to positions 101 and 108, respectively, in the mature IL-15 polypeptide, which lacks a 48-amino acid signal sequence.

Similarly, this strategy can be used to incorporate any other amino acid in place of the glutamine residues at positions 149 or 156 or to introduce amino acid substitutions at positions other than 149 and/or 156.

Proliferation of BAF-BO3 Cells in the Presence of IL-15 Related Proteins

The double mutant IL-15 polypeptide may inhibit BAF-BO3 proliferation in a dose-dependent manner: addition of 30 μl (approximately 50 μg/ml) of the double mutant IL-15 inhibited proliferation more completely than did addition of 20 μL of the same concentration of the double mutant IL-15.

Proliferation of PHA-Stimulated Human PBMCs

The ability of the FLAG-HMK-IL-15 double mutant polypeptide to bind PHA activated human PBMCs was demonstrated as follows. PHA-activated PBMCs were washed and incubated with medium alone, or with the FLAG-HMK-IL-15 double mutant. The cells were then incubated with an anti-FLAG biotinylated antibody and stained with streptavidin conjugated to RED670. The stained cells were analyzed by flow cytometry.

FACS Analysis of Leukemic Cell Lines Stained with Wild-Type FLAG-HMK-IL-15

In a series of experiments similar to those above, the ability of the wild-type FLAG-HMK-IL-15 polypeptide to bind leukemia cells was shown. The cells treated were obtained from the leukemic cell lines MOLT-14, YT, HuT-102, and from cell lines currently being established at Beth Israel Hospital (Boston, Mass.), and named 2A and 2B. The cultured cells were washed and incubated with either medium alone or with medium containing the FLAG-HMK-IL-15 wild-type polypeptide. The cells were then incubated with the biotinylated anti-FLAG antibody and stained with RED670-conjugated streptavidin. The stained cells were analyzed by flow cytometry.

Genetic Construction of Additional Mutant IL-15 Chimeric Polypeptides

In addition to the FLAG-HMK-IL-15 chimera, which provides the mutant IL-15 with an antigenic tag, numerous other polypeptides can be linked to any mutant of IL-15. For example, mutant IL-15 can be linked to the Fc fragment of the IgG subclass of antibodies according to the following method.

Genetic Construction of Mutant IL-15/Fc cDNA for Fcγ2a can be generated from mRNA extracted from an IgG2a secreting hybridoma using standard techniques with reverse transcriptase (MMLV-RT; Gibco-BRL, Grand Island, N.Y.) and a synthetic oligo-dT (12-18) oligonucleotide (Gibco BRL). The mutant IL-15 cDNA can be amplified from a plasmid template by PCR using IL-15 specific synthetic oligonucleotides.

The 5' oligonucleotide is designed to insert a unique NotI restriction site 40 nucleotides 5' to the translational start codon, while the 3' oligonucleotide eliminates the termination codon and modifies the C-terminal Ser residue codon usage from AGC to TCG to accommodate the creation of a unique BamHI site at the mutant IL-15/Fc junction. Synthetic oligonucleotides used for the amplification of the Fcγ2a domain cDNA change the first codon of the hinge from Glu to Asp in order to create a unique BamHI site spanning the first codon of the hinge and introduce a unique XbaI site 3' to the termination codon.

The Fc fragment can be modified so that it is non-target-cell depleting, i.e., not able to activate the complement system. To make the non-target-cell depleting mutant IL-15 construct (mIL-15/Fc), oligonucleotide site directed mutagenesis is used to replace the C'1q binding motif Glu318, Lys320, Lys322 with Ala residues. Similarly, Leu235 is replaced with Glu to inactivate the FcγR I binding site. Ligation of cytokine and Fc" components in the correct translational reading frame at the unique BamHI site yields a 1,236 basepair open reading frame encoding a single 411 amino acid polypeptide (including the 18 amino acid IL-15 signal peptide) with a total of 13 cysteine residues. The mature secreted homodimeric IL-15/Fc is predicted to have a total of up to eight intramolecular and three inter-heavy chain disulfide linkages and a molecular weight of approximately 85 kDa, exclusive of glycosylation.

Expression and Purification of mIL-15 Fc Fusion Proteins

Proper genetic construction of mIL-15/Fc can be confirmed by DNA sequence analysis following cloning of the fusion gene as a NotI-XbaI cassette into the eukaryotic expression plasmid pRc/CMV (Invitrogen, San Diego, Calif.). This plasmid carries a CMV promoter/enhancer, a bovine growth hormone polyadenylation signal and a neomycin resistance gene for selection with G418. Plasmids carrying the mIL-15/Fc fusion gene is transfected into Chinese hamster ovary cells (CHO-K1, available from the American Type Culture Collection) by electroporation (1.5 kV/3 µF/0.4 cm/PBS) and selected in serum-free Ultra-CHO media (BioWhittaker Inc., Walkerville, Md.) containing 1.5 mg/ml of G418 (Geneticin, Gibco BRL). After subcloning, clones that produce high levels of the fusion protein are selected by screening supernatants from IL-15 by ELISA (PharMingen, San Diego, Calif.). mIL-15/Fc fusion proteins are purified from culture supernatants by protein A sepharose affinity chromatography followed by dialysis against PBS and 0.22 µm filter sterilization. Purified proteins can be stored at −20° C. before use.

Western blot analysis following SDS-PAGE under reducing (with DTT) and non-reducing (without DTT) conditions can be performed using monoclonal or polyclonal anti-mIL-15 or anti Fcγ primary antibodies to evaluate the size and isotype specificity of the fusion proteins. The functional activity of mutant IL-15/Fc can be assessed by a standard T cell proliferation assay, as described above.

Administration of mIL-15 and CTLA4/Ig

The work that follows demonstrates that allograft survival is dramatically improved when an allograft recipient is treated with an agent that targets an IL-15R and an agent that blocks a costimulatory signal. Crude islet allografts were implanted in mice rendered diabetic by injection of streptozotocin. All allografts from DBA/2J(H-2d) donors to B6AF1(H-2b/d,k) recipients were accepted permanently when mice were treated with CTLA4/Ig and mIL-15/Fc. Permanent engraftment was never seen in untreated or single protein treated mice. Fully MHC mismatched islet allografts from Balb/c$^{(H2d)}$ to C57B1/6$^{(H2b)}$ were rejected with mean survival times of 15 days in untreated mice, 30 days in mice treated with CTLA4/Ig alone, and 30 days in mice with mIL-15Fc alone. In contrast, treatment with CTLA4/Ig and mIL-15/Fc led to permanent graft survival in more than 70% of treated mice (see also, FIG. 3). Moreover, a state of stable allograft tolerance was observed in two recipients that accepted a second Balb/c islet allograft without imunosuppressive treatment. Quantitative RT-PCR analysis of the graft tissues and lymph nodes also revealed a marked decrease in expression of T cell receptor transcripts as well as many lymphokine genes following combined treatment. Histologic analysis confirmed that combined treatment protected the graft from leukocytic infiltration.

What is claimed is:

1. A therapeutic composition comprising a first agent that targets an interleukin-15 receptor (IL-15R), wherein the first agent comprises a mutant IL-15 polypeptide that inhibits at least one of the cellular events that normally occurs when wild-type IL-15 specifically binds to an IL-15 receptor complex, the mutant IL-15 polypentide comprising a mutation at position 149 and position 156 of SEQ ID NO:4, and a second agent that inhibits a costimulatory signal transmitted between a T cell and an antigen-presenting cell (APC), wherein the second agent comprises a polypeptide that binds CD28.

2. The therapeutic composition of claim 1, wherein the polypeptide that binds CD28 comprises an anti-CD28 antibody.

3. The therapeutic composition of claim 1, wherein mutation at position 149 of SEQ ID NO:4 is a substitution of aspartate for glutamine.

4. The therapeutic composition of claim 1, wherein the mutation at position 156 of SEQ ID NO:4 is a substitution of aspartate for glutamine.

5. A method of suppressing an immune response in a patient, the method comprising administering to the patient a therapeutic composition comprising a first agent that targets an IL-15 R, wherein the first agent comprises a mutant IL-15 R, polypeptide that inhibits at least one of the cellular events that normally occurs when wild-type IL-15 specifically binds to an IL-15 receptor complex, the mutant IL-15 polypeptide comprising a mutation at position 149 and position 156 of SEQ ID NO:4, and a second agent that inhibits a costimulatory signal transmitted between a T cell and an antigen presenting cell (APC), wherein the second agent comprises a polypeptide that binds CD28.

6. The method of claim 5, wherein the patient has an immune disease, particularly an autoimmune disease, or is at risk of developing an immune disease, particularly an autoimmune disease.

7. The method of claim 6, wherein the autoimmune disease is a rheumatic disease selected from the group consisting of systemic lupus erythematosus, Sjögren's syndrome, scleroderma, mixed connective tissue disease, dermatomyositis, polymyositis, Reiter's syndrome, and Bechet's disease.

8. The method of claim 6, wherein the autoimmune disease is rheumatoid arthritis.

9. The method of claim 6, wherein the autoimmune disease is type I diabetes.

10. The method of claim 6, wherein the autoimmune disease is an autoimmune disease of the thyroid selected from the group consisting of Hashimoto's thyroiditis and Graves' Disease.

11. The method of claim 6, wherein the autoimmune disease is an autoimmune disease of the central nervous system selected from the group consisting of multiple sclerosis, myasthenia gravis, and encephalomyelitis.

12. The method of claim 6, wherein the autoimmune disease is a variety of phemphigus selected from the group consisting of phemphigus vulgaris, phemphigus vegetans, phemphigus foliaceus, Senear-Usher syndrome, and Brazilian phemphigus.

13. The method of claim 6, wherein the autoimmune disease is psoriasis.

14. The method of claim 6, wherein the autoimmune disease is inflammatory bowel disease.

15. The method of claim 6, wherein the patient has received a transplant of a biological organ, tissue, or cell.

16. The method of claim 6, wherein the patient has received a vascular injury.

17. The method of claim 6, wherein the patient has type II diabetes.

* * * * *

UNITED STATES PATENT AND TRADEMARK OFFICE
CERTIFICATE OF CORRECTION

PATENT NO. : 7,347,995 B2
APPLICATION NO. : 10/853466
DATED : March 25, 2008
INVENTOR(S) : Terry B. Strom et al.

It is certified that error appears in the above-identified patent and that said Letters Patent is hereby corrected as shown below:

In column 12, line 56, delete the first, second and third occurrence of "phemphigus" and insert --pemphigus--

In column 12, line 57, delete "phemphigus" and insert

--pemphigus--

In column 12, line 58, delete "phemphigus" and insert

--pemphigus--

In claim 1, column 25, line 50, delete "polypentide" and insert

--polypeptide--

In claim 1, column 25, line 51, delete "NO:4,and" and insert

--NO:4, and--

In claim 5, column 26, line 45, delete "IL-15 R," and insert

--IL-15--

In claim 5, column 26, line 49, delete "SEO" and insert

--SEQ--

In claim 7, column 26, line 63, delete "Bechet's" and insert

--Behcet's--

In claim 12, column 27, line 10, delete "phemphigus" and insert

--pemphigus--

In claim 12, column 27, line 11, delete the first and second occurrence of "phemphigus"

and insert --pemphigus--

UNITED STATES PATENT AND TRADEMARK OFFICE
CERTIFICATE OF CORRECTION

PATENT NO. : 7,347,995 B2
APPLICATION NO. : 10/853466
DATED : March 25, 2008
INVENTOR(S) : Terry B. Strom et al.

It is certified that error appears in the above-identified patent and that said Letters Patent is hereby corrected as shown below:

In claim 12, column 27, line 12, delete "phemphigus" and insert

--pemphigus--

In claim 12, column 27, line 13, delete "phemphigus" and insert

--pemphigus--

Signed and Sealed this

Eighth Day of July, 2008

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 489
<212> TYPE: DNA
<213> ORGANISM: Homo sapiens
<220> FEATURE:
<221> NAME/KEY: CDS
<222> LOCATION: (1)...(486)

<400> SEQUENCE: 1 atg aga att tcg aaa cca cat ttg aga agt att tcc atc cag tgc tac      48
Met Arg Ile Ser Lys Pro His Leu Arg Ser Ile Ser Ile Gln Cys Tyr
  1               5                  10                  15 ttg tgt tta ctt cta aac agt cat ttt cta act gaa gct ggc att cat      96
Leu Cys Leu Leu Leu Asn Ser His Phe Leu Thr Glu Ala Gly Ile His
              20                  25                  30
```

```
gtc ttc att ttg ggc tgt ttc agt gca ggg ctt cct aaa aca gaa gcc    144
Val Phe Ile Leu Gly Cys Phe Ser Ala Gly Leu Pro Lys Thr Glu Ala
         35                  40                  45 aac tgg gtg aat gta ata agt gat ttg aaa aaa att gaa gat ctt att    192
Asn Trp Val Asn Val Ile Ser Asp Leu Lys Lys Ile Glu Asp Leu Ile
 50                  55                  60 caa tct atg cat att gat gct act tta tat acg gaa agt gat gtt cac    240
Gln Ser Met His Ile Asp Ala Thr Leu Tyr Thr Glu Ser Asp Val His
 65                  70                  75                  80 ccc agt tgc aaa gta aca gca atg aag tgc ttt ctc ttg gag tta caa    288
Pro Ser Cys Lys Val Thr Ala Met Lys Cys Phe Leu Leu Glu Leu Gln
                 85                  90                  95 gtt att tca ctt gag tcc gga gat gca agt att cat gat aca gta gaa    336
Val Ile Ser Leu Glu Ser Gly Asp Ala Ser Ile His Asp Thr Val Glu
             100                 105                 110 aat ctg atc atc cta gca aac aac agt ttg tct tct aat ggg aat gta    384
Asn Leu Ile Ile Leu Ala Asn Asn Ser Leu Ser Ser Asn Gly Asn Val
         115                 120                 125 aca gaa tct gga tgc aaa gaa tgt gag gaa ctg gag gaa aaa aat att    432
Thr Glu Ser Gly Cys Lys Glu Cys Glu Glu Leu Glu Glu Lys Asn Ile
130                 135                 140 aaa gaa ttt ttg gac agt ttt gta cat att gtc gac atg ttc atc aac    480
Lys Glu Phe Leu Asp Ser Phe Val His Ile Val Asp Met Phe Ile Asn
145                 150                 155                 160 act tct tga                                                         489
Thr Ser

<210> SEQ ID NO 2
<211> LENGTH: 162
<212> TYPE: PRT
<213> ORGANISM: Homo sapiens

<400> SEQUENCE: 2

Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
             100                 105                 110

Asn Leu Ile Ile Leu Ala Asn Asn Ser Leu Ser Ser Asn Gly Asn Val
         115                 120                 125

Thr Glu Ser Gly Cys Lys Glu Cys Glu Glu Leu Glu Glu Lys Asn Ile
130                 135                 140

Lys Glu Phe Leu Asp Ser Phe Val His Ile Val Asp Met Phe Ile Asn
145                 150                 155                 160

Thr Ser

<210> SEQ ID NO 3
<211> LENGTH: 489
<212> TYPE: DNA
```

```
<213> ORGANISM: Homo sapiens
<220> FEATURE:
<221> NAME/KEY: CDS
<222> LOCATION: (1)...(486)

<400> SEQUENCE: 3 atg aga att tcg aaa cca cat ttg aga agt att tcc atc cag tgc tac      48
Met Arg Ile Ser Lys Pro His Leu Arg Ser Ile Ser Ile Gln Cys Tyr
 1               5                  10                  15 ttg tgt tta ctt cta aac agt cat ttt cta act gaa gct ggc att cat      96
Leu Cys Leu Leu Leu Asn Ser His Phe Leu Thr Glu Ala Gly Ile His
             20                  25                  30 gtc ttc att ttg ggc tgt ttc agt gca ggg ctt cct aaa aca gaa gcc     144
Val Phe Ile Leu Gly Cys Phe Ser Ala Gly Leu Pro Lys Thr Glu Ala
         35                  40                  45 aac tgg gtg aat gta ata agt gat ttg aaa aaa att gaa gat ctt att     192
Asn Trp Val Asn Val Ile Ser Asp Leu Lys Lys Ile Glu Asp Leu Ile
     50                  55                  60 caa tct atg cat att gat gct act tta tat acg gaa agt gat gtt cac     240
Gln Ser Met His Ile Asp Ala Thr Leu Tyr Thr Glu Ser Asp Val His
 65                  70                  75                  80 ccc agt tgc aaa gta aca gca atg aag tgc ttt ctc ttg gag tta caa     288
Pro Ser Cys Lys Val Thr Ala Met Lys Cys Phe Leu Leu Glu Leu Gln
                 85                  90                  95 gtt att tca ctt gag tcc gga gat gca agt att cat gat aca gta gaa     336
Val Ile Ser Leu Glu Ser Gly Asp Ala Ser Ile His Asp Thr Val Glu
            100                 105                 110 aat ctg atc atc cta gca aac aac agt ttg tct tct aat ggg aat gta     384
Asn Leu Ile Ile Leu Ala Asn Asn Ser Leu Ser Ser Asn Gly Asn Val
        115                 120                 125 aca gaa tct gga tgc aaa gaa tgt gag gaa ctg gag gaa aaa aat att     432
Thr Glu Ser Gly Cys Lys Glu Cys Glu Glu Leu Glu Glu Lys Asn Ile
    130                 135                 140 aaa gaa ttt ttg cag agt ttt gta cat att gtc caa atg ttc atc aac     480
Lys Glu Phe Leu Gln Ser Phe Val His Ile Val Gln Met Phe Ile Asn
145                 150                 155                 160 act tct tga                                                         489
Thr Ser

<210> SEQ ID NO 4
<211> LENGTH: 162
<212> TYPE: PRT
<213> ORGANISM: Homo sapiens

<400> SEQUENCE: 4

Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110
```

```
Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 5
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 5
ggaattcaac tgggtgaatg taata                                             25

<210> SEQ ID NO 6
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 6
cgggatcctc aagaagtgtt gatgaa                                            26

<210> SEQ ID NO 7
<211> LENGTH: 60
<212> TYPE: DNA
<213> ORGANISM: Artificial Sequence
<220> FEATURE:
<223> OTHER INFORMATION: Synthetically generated oligonucleotide

<400> SEQUENCE: 7
cgggatcctc aagaagtgtt gatgaacatg tcgacaatat gtacaaaact gtccaaaaat       60
```